United States Patent
Yamanishi et al.

(10) Patent No.: US 11,427,807 B2
(45) Date of Patent: Aug. 30, 2022

(54) SERUM-FREE MEDIUM CONTAINING PDGF FOR DS CELLS

(71) Applicant: Shiseido Company, Ltd., Tokyo (JP)

(72) Inventors: Haruyo Yamanishi, Yokohama (JP); Tsutomu Soma, Yokohama (JP); Yuzo Yoshida, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 79 days.

(21) Appl. No.: 15/643,869

(22) Filed: Jul. 7, 2017

(65) Prior Publication Data

US 2017/0313982 A1    Nov. 2, 2017

Related U.S. Application Data

(62) Division of application No. 14/897,312, filed as application No. PCT/JP2014/065599 on Jun. 12, 2014, now abandoned.

(30) Foreign Application Priority Data

Jun. 12, 2013  (JP) .............................. JP2013-123263

(51) Int. Cl.
    *C12N 5/071*    (2010.01)

(52) U.S. Cl.
    CPC ......... *C12N 5/0625* (2013.01); *C12N 5/0628* (2013.01); *C12N 2500/90* (2013.01); *C12N 2501/135* (2013.01)

(58) Field of Classification Search
    None
    See application file for complete search history.

(56) References Cited

U.S. PATENT DOCUMENTS

| 7,635,589 B2 | 12/2009 | Park | |
|---|---|---|---|
| 2006/0088505 A1* | 4/2006 | Hoffmann | C12N 5/0628 424/93.7 |
| 2007/0212335 A1* | 9/2007 | Hantash | A61L 27/3869 424/93.7 |
| 2010/0197019 A1 | 8/2010 | Toyoshima et al. | |
| 2010/0311163 A1 | 12/2010 | Ishimatsu et al. | |

FOREIGN PATENT DOCUMENTS

| JP | 2005-218445 A | 8/2005 | |
|---|---|---|---|
| JP | 2009-171852 A | 8/2009 | |
| WO | WO 03/064598 A2 | 8/2003 | |
| WO | WO 2006/057542 A1 | 6/2006 | |
| WO | WO 2007/037486 A1 | 4/2007 | |
| WO | WO 2011/159359 A2 | 12/2011 | |
| WO | WO-2012036211 A1 * | 3/2012 | ............. C12Q 1/686 |

OTHER PUBLICATIONS

Kamp, H. et al. 2003. Regulation of PDGF and PDGF receptor in cultured dermal papilla cells and follicular keratinocytes of the human hair follicle. Experimental Dermatology 12: 662-672. specif, pp. 662, 663, 664, 670.*
Chase, L.G. et al. 2010. A novel serum-free medium for the expansion of human mesenchymal stem cells. Stem Cell Research & Therapy 1(8): 1-11. specif, pp. 1, 2, 7, 8, 10.*
Soma, T. et al. Jan. 27, 2012. Hair-inducing ability of human dermal papilla cells cultured under Wnt/B-catenin signalling activation. Experimental Dermatology 21: 307-309. specif, pp. 307, 308, 309.*
McElwee, K.J. et al. 2003. Cultured peribulbar dermal sheath cells can induce hair follicle development and contribute to the dermal sheath and dermal papilla. Journal of Investigative Dermatology 121: 1267-1275. specif. pp. 1267, 1268, 1269, 1271, 1274.*
EngMT—Soma, T. et al. (WO 2012) Skin activation by means of PDGF-BB activity enhancement. International Patent Application Publication No. WO 2012/036211 A1, pp. 1-11. specif, pp. 2, 5, 6, 7, 10.*
Driskell, R.R. et al. 2011. Hair follicle dermal papilla cells at a glance. Journal of Cell Science 124: 1179-1182. specif. pp. 1179, 1181.*
Arora, M. 2013. Cell culture media: a review. Materials and Methods 3(175). Last modified: Aug. 26, 2021. Downloaded on: Sep. 23, 2021. Retrieved from: <https://www.labome.com/method/Cell-Culture-Media-A-Review.html> pp. 1-19; specif. pp. 1, 5.*
DcDiagnoCine. HFDM-1 medium. Datasheet [online]. Copyright Diagnocine. Retrieved on Sep. 24, 2021. Downloaded from the internet: <https://diagnocine.com/Product/HFDM1-Medium-Synthetic-medium-for-human-fibroblast/53104> pp. 1-6; specif. p. 3.*
Abe, Takashi, Ph.D., "Kinosei Keshohin no Kenkyu Kaihatsu Doko," Fragrance Journal, 2007, 35(2): 108-112.
Kamp et al., "Regulation of PDGF and PDGF receptor in cultured dermal papilla cells and follicular keratinocytes of the human hair follicle," Experimental Dermatology, 2003, 12:662-672.
Miyakura et al., "The influence of extracellular matrix and growth factors on early hair follicle development using hair patch assay," J. Tokyo Med. Univ., 2011, 69(2):210-218.
Osawa et al., "Stem cells in the mammalian hair follicle," Protein, Nucleic Acid and Enzyme, 2004, 49(6):727-733.
Tomita et al., "PDGF isoforms induce and maintain anagen phase of murine hair follicles," Journal of Dermatological Science, 2006, 43(2):105-115.

* cited by examiner

*Primary Examiner* — Olivia M. Wise
*Assistant Examiner* — Sharon M. Papciak
(74) *Attorney, Agent, or Firm* — Foley & Lardner LLP

(57) ABSTRACT

The present disclosure relates to a serum-free medium for culturing of DS cells containing platelet derived growth factor (PDGF), or to a method for culturing of dermal sheath (DS) cells, using serum-free medium comprising PDGF.

6 Claims, 10 Drawing Sheets

| Medium | Lifetechnologies StemProSFM CTS (sup+) | Lifetechnologies StemProSFM CTS (sup+), PDGF-BB 10ng/ml | BD Mosaic sup(+) | BD Mosaic sup(+) PDGF-BB 10ng/ml |
|---|---|---|---|---|
| Day 2 | | | | |
| Day 7 | | | | |

FIG. 5

| Medium | CSTI HFDM1(-) | CSTI HFDM(+) | CSTI HFDM1(-) PDGF-AA 10ng/ml | CSTI HFDM1(-) PDGF-BB 10ng/ml |
|---|---|---|---|---|
| Day 2 | | | | |
| Day 7 | | | | |

| Medium | Lifetechnologies StemProSFM CTS (sup+) | Lifetechnologies StemProSFM CTS (sup+), PDGF-BB 10ng/ml |
|---|---|---|
| Day 2 | | |
| Day 7 | | |

SERUM-FREE MEDIUM CONTAINING PDGF FOR DS CELLS

CROSS-REFERENCE TO RELATED APPLICATIONS

This application is a Divisional of U.S. application Ser. No. 14/897,312, which is a National Stage application of PCT/JP2014/065599, filed Jun. 12, 2014, which claims priority from Japanese application JP 2013-123263, filed Jun. 12, 2013.

TECHNICAL FIELD

The present invention relates to a serum-free medium for culturing of DS cells, comprising platelet-derived growth factor (PDGF), and to a method for culturing of dermal sheath (DS) cells, using serum-free medium comprising PDGF.

BACKGROUND ART

Hair is considered very important for aesthetic outer appearance. Therefore, alopecia or hair loss due to congenital or acquired causes can be seriously distressing for individuals. Particularly in modern society, which has been referred to as an "aging society" or "stress society", there is increasing risk of alopecia of head hair due to a variety of acquired causes. Many attempts have been made in response to this situation, to provide cosmetic or medical methods for safely and effectively regenerating hair follicles in individuals suffering from alopecia or hair loss.

Hair follicles are exceptional organs that repeat self-regeneration in the mature body essentially throughout the entire lifetime. Elucidating the mechanism of this self-regeneration is expected to lead to highly demanded clinical applications, such as alopecia treatment by transplantation of tissue or cells, or construction of near-natural, highly functional skin sheets that include hair follicles and sebaceous glands. In recent years, with increasing interest in stem cell research and the rapid progress in research on follicular epithelial stem cells (epithelial cells), a greater understanding has been reached in regard to the properties of hair papilla cells, as hair follicle-specific mesenchymal cells. Hair papilla cells perform the role of "control towers", that is, of sending activation signals to follicular epithelial stem cells for self-regeneration of hair follicles, and have been found to be essential cells, together with follicular epithelial stem cells, in the hair follicle reconstitution evaluation system (Kishimoto et al., Proc. Natl. Acad. Sci. USA (1999), Vol. 96, pp. 7336-7341; NPL 1).

Hair papilla (or dermal papilla, DP) and the dermal sheath (DS) surrounding hair follicles, are both composed of mesenchymal cell groups, unlike the epithelial cells forming the major portions of the hair follicles. Recently there have been many reports of new findings suggesting the importance of DS cells in hair follicle formation. It has been reported that in hair bulb-cutting hair follicle transplant experiments with hair papilla rat whiskers, DP cells are regenerated from DS cells, and that in mice, hair follicle regeneration is induced by transplanting DS cells from hair follicles that have been cut at the lower half. Also, Jahoda et al. (Development. 1992 April:114(4): 887-97; NPL 2) have reported that reconstruction of hair follicles can be induced by transplanting DS cells in humans (Horne K A and Jahoda C A. Development. 1992 November:116(3): 563-71; NPL 3). Further, the group of Tobin, Paus et al. has reported that in the mouse hair cycle, cell migration takes place between DS cells and DP cells, and that proliferation of DS cells begins before DP cells, whose proliferation begins in the hair growth cycle (Tobin D J et al., J. Invest. Dermatol., 120:895-904, 2003; NPL 4).

Thus, while it is highly possible that DS cells play an important role in hair follicle formation, the action mechanism has not yet been fully elucidated. It is necessary to obtain large amounts of DS cells in order to shed light on the action mechanism for hair follicle formation, but because of the small number of cells that can be harvested from biological tissue, it becomes necessary to accomplish efficient growth by in vitro culturing of the cells. For culturing of DS cells it is common to use serum-added medium that promotes cell growth and binding to the culture vessel, but since antigenic variation and pathogenic contamination can potentially occur under such conditions, and variation may arise in the experimental results due to unidentifiable trace components in the serum, it is unsuitable for clinical applications for regenerative medicine or for drug development or toxicity test applications.

With the increasing interest in regenerative medicine in recent years, culturing methods and culturing media have been developed for mesenchymal stem cells (see Japanese Unexamined Patent Publication No. 2006-311814; PTL 1, Japanese Unexamined Patent Publication No. 2006-325445; PTL 2, and Japanese Unexamined Patent Publication No. 2005-151237; PTL 3, for example), but a serum-free medium containing platelet-derived growth factor (PDGF) for culturing of DS cells remains yet unknown.

CITATION LIST

Patent Literature

[PTL 1] Japanese Unexamined Patent Publication No. 2006-311814
[PTL 2] Japanese Unexamined Patent Publication No. 2006-325445
[PTL 3] Japanese Unexamined Patent Publication No. 2005-151237
[PTL 4] Japanese Unexamined Patent Publication HEI No. 7-274950

Non-Patent Literature

[NPL 1] Kishimoto et al., Proc. Natl. Acad Sci. USA (1999), Vol. 96, pp. 7336-7341
[NPL 2] Jahoda C A et al., Development. 1992 April; 114 (4):887-97. [NPL 3] Horne K A and Jahoda C A. Development. 1992 November; 116(3):563-71.
[NPL 4] Tobin D J et al., J. Invest. Dermatol., 120:895-904, 2003
[NPL 5] Noburo Sato et al., Nature Medicine Vol. 10, No. 1, January 2004

DISCLOSURE OF THE INVENTION

Problems to be Solved by the Invention

It is an object of the present invention to provide a serum-free medium suitable for culturing of DS cells.

Means for Solving the Problems

The present inventors have acquired the surprising knowledge that it is possible to significantly grow DS cells by culturing in serum-free medium containing added PDGF, and particularly PDGF-BB.

The present invention therefore encompasses the following.

[1] A serum-free medium for culturing of dermal sheath (DS) cells, comprising platelet-derived growth factor (PDGF).

[2] The serum-free medium according to [1], wherein the PDGF is PDGF-BB.

[3] The serum-free medium according to [1] or [2], wherein the dermal sheath (DS) cells are derived from the dermal sheath cup (DSC) region.

[4] A method for culturing dermal sheath (DS) cells, using a serum-free medium comprising platelet-derived growth factor (PDGF).

[5] The method according to [4], wherein the PDGF is PDGF-BB.

[6] The method according to [4] or [5], wherein the dermal sheath (DS) cells are derived from the dermal sheath cup (DSC) region.

Effect of the Invention

The serum-free medium of the invention allows efficient culturing of DS cells suitable for clinical applications in regenerative medicine or applications for drug development or toxicity testing.

BRIEF DESCRIPTION OF THE DRAWINGS

FIG. 1 is a photomicrograph of human DS cells cultured using 1) HFDM-1(−) medium, 2) HFDM-1(+) medium, 3) PDGF-AA (10 ng/ml)-dissolved HFDM-1(−) medium and 4) PDGF-BB (10 ng/ml)-dissolved HFDM-1(−) medium, as serum-free media, on days 2 and 10.

FIG. 3 is a photomicrograph of human DS cells cultured using 1) StemProSFM CTS (sup+, Life Technologies), 2) PDGF-BB (10 ng/ml)-dissolved StemProSFM CTS (sup+, Life Technologies), 3) Mosaic hMSC SF Culture Medium (sup+, BD) and 4) PDGF-BB (10 ng/ml)-dissolved Mosaic hMSC SF Culture Medium (sup+, BD), as serum-free medium, on days 2 and 7.

FIG. 5 is a photomicrograph of human DS cells cultured using 1) HFDM-1(−) medium, 2) HFDM-1(+) medium, 3) PDGF-AA (10 ng/ml)-dissolved HFDM-1(−) medium and 4) PDGF-BB (10 ng/ml)-dissolved HFDM-1(−) medium, as serum-free media, on days 2 and 7.

FIG. 7 is a photomicrograph of human DS cells cultured using 1) StemProSFM CTS (sup−, Life Technologies), 2) PDGF-BB (10 ng/ml)-dissolved StemProSFM CTS (sup−, Life Technologies), 3) StemProSFM CTS (sup+, Life Technologies) and 4) PDGF-BB (10 ng/ml)-dissolved StemProSFM CTS (sup+, Life Technologies), as serum-free media, on days 2 and 7.

FIG. 9 is a photomicrograph of human skin fibroblasts cultured using 1) StemProSFM CTS (sup+, Life Technologies) and 2) PDGF-BB (10 ng/ml)-dissolved StemProSFM CTS (sup+, Life Technologies), as serum-free media, on days 2 and 7.

Figure 2:
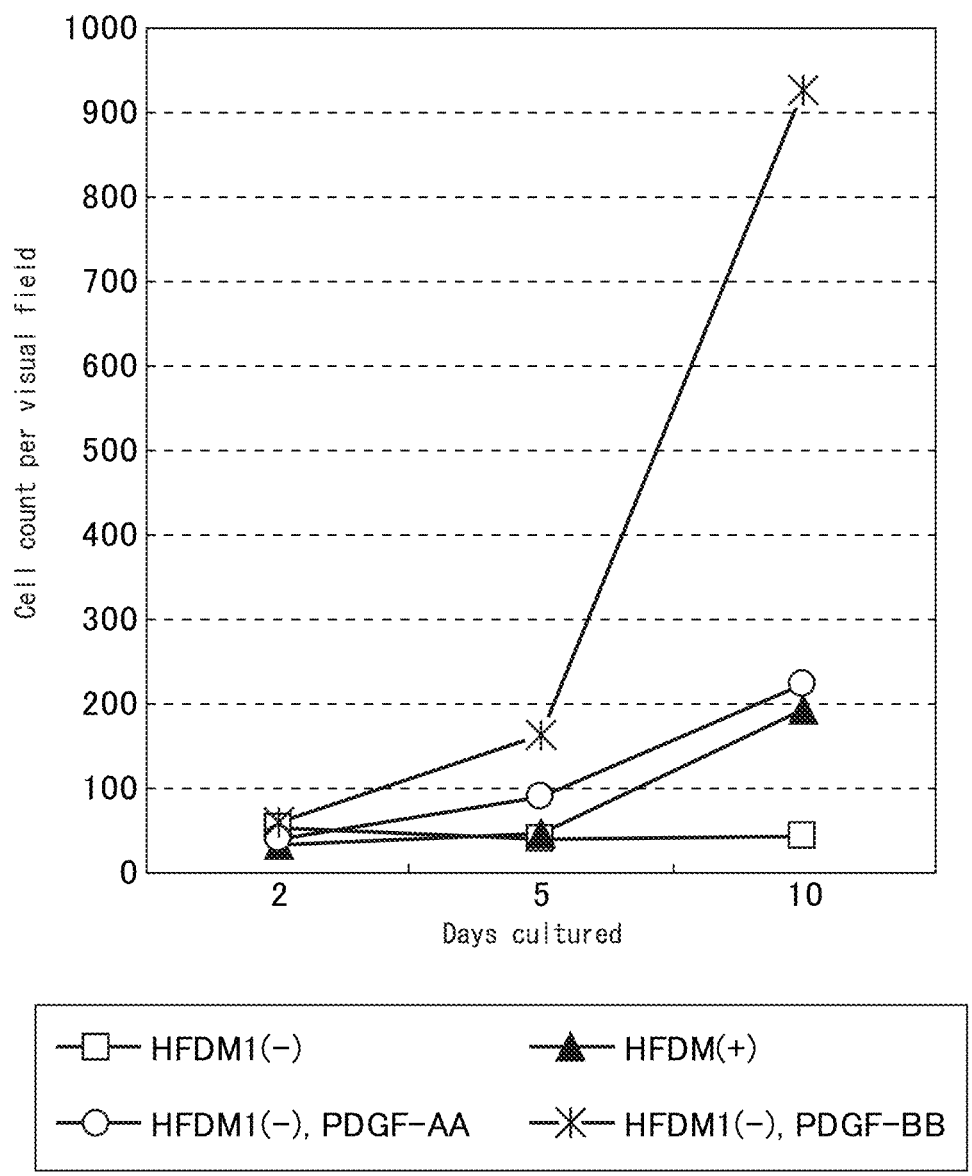
FIG. 2 is a graph showing changes in cell counts of human DS cells cultured using 1) HFDM-1(−) medium, 2) HFDM-1(+) medium, 3) PDGF-AA (10 ng/ml)-dissolved HFDM-1(−) medium and 4) PDGF-BB (10 ng/ml)-dissolved HFDM-1(−) medium, as serum-free media (days 2, 5 and 10).

The present invention provides a serum-free medium for culturing of dermal sheath DS cells, the serum-free medium containing platelet-derived growth factor (PDGF) and particularly PDGF-BB, and to a method of culturing DS cells using the serum-free medium.

Dermal sheath (DS) cells are a mesenchymal cell type present in the dermal sheath. The dermal sheath (DS), also known as connective-tissue hair sheath or connective-tissue sheath, is the dermal tissue surrounding the epithelial outer root sheath. DS cells are classified as mesenchymal cells, similar to hair papilla (dermal papilla, or DP) cells, with DP cells being thought to derive from DS cells. Within the dermal sheath (DS), the cells derived from the dermal sheath cup (DSC) region in particular, which is the basal region near the hair papilla, proliferate before proliferation of DP cells during the hair growth cycle, and it is therefore believed that DS cells, and especially cells derived from the DSC region (also referred to as "DSC cells") are the source of DP cells (Tobin D J et al., J. Invest. Dermatol., 120:895-904, 2003; NPL 4). The dermal sheath, and especially the DSC region, is composed of a hetero cell group, and it is believed that these undergo descent with cell division and migration from the resting phase to the growth phase of the hair cycle, a portion thereof differentiating to hair papilla DP and initiating elongation of hair.

The DS cells of the invention can be obtained from the epidermis of various mammal such as humans, chimpanzees and other primates, livestock animals such as dogs, cats, rabbits, horses, sheep, goats, cows and pigs, and experimental animals such as rats, mice and guinea pigs, and more preferably nude mice, SCID mice and nude rats, but they are preferably human-derived cells, from the viewpoint of transplantation in humans and production of three-dimensional models for research. Also, the epidermal region may be a hairy region such as the scalp, or a hairless region such as the prepuce.

Also, the DS cells may be cells obtained by primary culturing of tissue of the aforementioned mammals, or cells obtained from subculturing, or cells obtained by inducing differentiation from somatic stem cells, iPS cells or ES cells. From the viewpoint of conducting transplantation, cells grown by subculturing of cells obtained from the object of transplantation are preferred.

The basal medium that may be used for the invention is not particularly restricted so long as it is serum-free medium used for culturing of human or animal cells. Various types of serum-free media are commercially available, and include for example, HFDM-1(+) (Cell Science & Technology Institute), HFDM-1(−) (Cell Science & Technology Institute), StemPro MSC SFM CTS (sup+) (Life Technologies), StemPro MSC SFM CTS (sup−) (Life Technologies), Mosaic hMSC SF Culture Medium (sup+) (BD) and the like. Regarding the compositions of these commercially available media, HFDM-1(−) contains basal medium RITC80-7, 5 μg/ml, insulin and $10^{-7}$ M dexamethasone, and HFDM-1(+) contains, in addition to the above, 10 ng/ml EGF.

The serum-free medium of the invention contains platelet-derived growth factor (PDGF) as a growth factor for DS cells. PDGF is a growth factor mainly involved in modulating migration and growth of mesenchymal cells (fibroblasts, smooth muscle cells, glial cells and the like), and it belongs to the PDGF/VEGF family. Being mainly produced by megakaryocytes, it is also present in platelet α-granules, and is known to be produced by various cells such as epithelial cells and endothelial cells. At least 4 types of PDGF exist: PDGF-A, B, C and D, based on the A-chain, B-chain, C-chain or D-chain. All of these form homodimers or heterodimers, and five isoforms, PDGF-AA, -AB, -BB, -CC and -DD, are known to exist. PDGF-BB is particularly preferred among these.

There are no particular restrictions on the amount of PDGF added to the basal medium, and for example, it may be about 0.01 ng/ml to 10 μg/ml, preferably about 0.1 ng/ml to 100 ng/ml and more preferably about 1 to 10 ng/ml.

The serum-free medium of the invention may also contain an added Wnt signal activating agent. The Wnt signal is a series of actions that promote nuclear localization of β-catenin and exhibit function as a transcription factor. The signal includes a cascade due to intercellular interaction, when for example, the proteinWnt3A secreted from certain cells acts on other cells, causing nuclear localization of intracellular β-catenin, and leading to activity as a transcription factor. The cascade brings about the initial phenomenon of organ assembly, of which epithelium mesenchymal interaction is a typical example. The Wnt signal is known to control various cell functions such as cell motility during cellular growth and differentiation, organogenesis and early development, by activation of three pathways, the β-catenin pathway, PCP pathway and $Ca^{2+}$ pathway. It is utilized during culturing of ES cells, for the purpose of controlling differentiation, by the undifferentiated state-maintaining function of the Wnt signal (see Noburo Sato et al., Nature Medicine Vol. 10, No. 1, January 2004; NPL 5, for example).

There are no particular restrictions on the Wnt signal-activating agent, but any one exhibiting glycogen synthase kinase-3 (GSK-3) inhibitory activity may be used, examples of which include the bis-indolo(indirubin) compound (BIO) ((2'Z,3'E)-6-bromoindirubin-3'-oxime), its acetoxime analog BIO-acetoxime (2'Z, 3'E)-6-bromoindirubin-3'-acetoxime, the thiadiazolysine (TDZD) analog (4-benzyl-2-methyl-1,2,4-thiadiazolysine-3,5-dione), the oxothiadiazolysine-3-thione analog (2,4-dibenzyl-5-oxothiadiazolysine-3-thione), the thienyl-α-chloromethyl ketone compound (2-chloro-1-(4,4-dibromo-thiophen-2-yl)-ethanone), the phenyl-α-bromomethyl ketone compound (α-4-dibromoacetophenone), the thiazole-containing urea compound (N-(4-methoxybenzyl)-N'-(5-nitro-1,3-thiazol-2-yl) urea), or GSK-3β peptide inhibitors such as H-KEAPPAPPQSpP-NH$_2$, as well as lithium chloride and the like.

There are no particular restrictions on the amount of addition of the Wnt signal activating agent, and it may be any amount that leads to Wnt signal activation, or in other words, that produces GSK-3 inhibition and does not halt cell proliferation, which will depend on the type of chemical agent used and the type of cells to be grown, and may be appropriately determined by a person skilled in the art. For example, when BIO is used as the Wnt signal activating agent in DS cells, the amount may be, for example, about 0.01 μM to 100 μM, preferably 0.1 μM to 10 μM and more preferably about 10 μM.

Also, if necessary, the serum-free medium of the invention may contain added cell growth factors, hormones or other trace nutrients. Specific examples of these include epithelial growth factor (EGF), tumor necrosis factor-α (TNFα), hepatocyte growth factor (HGF), fibroblast growth factor 7 (FGF7), vascular endothelial growth factor (VEGF), basic fibroblast growth factor (bFGF), transforming growth factors β1, 2, 3 (TGFβ1, 2, 3), bone morphogenetic protein (BMP) and insulin-like growth factor-1, 2 (IGF-1, 2), in which case the amounts may be about 0.1 μg/ml to 100 μg/ml, for example. When a phospholipid (such as phosphatidic acid, phosphatidylinositol or ethanolamine) is used, the amount may be about 0.1 μg/ml to 100 μg/ml, for example. When a fatty acid (such as linolic acid, oleic acid or arachidonic acid) is used, the amount may be about 0.001 μg/ml to 100 μg/ml, for example. When a prostaglandin is used, the amount may be about 0.1 ng/ml-100 ng/ml, for example. When a reducing agent (such as ascorbic acid or reductive glutathione) is used, the amount may be about 1 μg/ml to 100 μg/ml, for example. When mercaptoethanol is used, the amount may be about 0.1 μg/ml to 100 μg/ml, for example. When transferrin or insulin is used, the amount may be about 0.01 μg/ml to 100 μg/ml. When dexamethasone is used, the amount may be about 0.000001 μM to 0.1 μM. When triiodothyronine is used, the amount may be about 0.1 pM to 100 pM. When glucagon is used, the amount may be about 0.0001 μM to 0.1 μM. When cholesterol is used, the amount may be about 0.1 μg/ml to 100 μg/ml, for example. When hydrocortisone is used, the amount may be about 0.01 μg/ml to 10 μg/ml, for example. When testosterone is used, the amount may be about 0.1 μM to 100 μM, for example. When estradiol or progesterone is used, the amount may be about 0.01 ng/ml to 100 ng/ml, for example. When a trace element (for example, copper, zinc, cobalt, manganese, molybdenum or selenium) is used, the amount may be about 0.000001 mg/ml to 0.1 mg/ml, for example. When albumin, fibronectin or vitronectin is used, the amount may be about 0.1 μg/ml to 1000 μg/ml, for example.

Culturing of DS cells in such serum-free media is usually carried out using a culture dish set in an incubator at 37° C. in an atmosphere of 5% $CO_2$, the culturing being continued (subculturing) after medium exchange upon confirming outgrowth. The cultured cells obtained in this manner are further subcultured for the necessary passage number. The subculturing may be carried out until the desired amount of DS cells is reached, and for example, 10 or more subculturings may be carried out, or if the desired amount is greater, preferably 15 or more and even more preferably 20 or more subculturings may be carried out.

Preferably, the DS cells cultured in this manner are allowed to form a sphere (Japanese Unexamined Patent Publication HEI No. 7-274950; PTL 4). Sphere formation produces cell growth to a saturated state, and after detachment of the cells, they are suspended in medium and the cell suspension is plated on medium in a non-adhesion-treated culture dish and allowed to stand for several days to form a cell aggregate consisting of a cell mass (spheroid). Preferably, the sphere formation is carried out in the absence of bFGF, although sufficient sphere formation can be achieved even in the presence of bFGF. There are no particular restrictions on the phase in which sphere formation is accomplished, and it may be carried out on cultured cells that have passed through the final subculture. Known culturing methods for formation of spheroids include roller bottle culturing, spinner flask culturing and hanging drop culturing, and culture vessels with recesses or culture vessels treated with low-cellular-adhesion coatings are commercially available. Also, by culturing using a culture vessel coated so that cell-adherent regions and non-cell-adherent regions are co-present, using a phosphorylcholine (PC)-based coating for the non-cell-adherent regions, it is possible to form large numbers of spheroids with consistent sizes.

The sphericized DS cells prepared in this manner maintain hair follicle inducing ability and are therefore useful for in vitro experiments in research to elucidate the mechanisms of hair follicle reconstitution, or for hair regenerative medicine.

The present invention will now be explained in greater detail by examples.

EXAMPLES

Example 1. Growth of DS Cells (Cup Region) Using Serum-Free Medium (HFDM-1)

Figure 1:
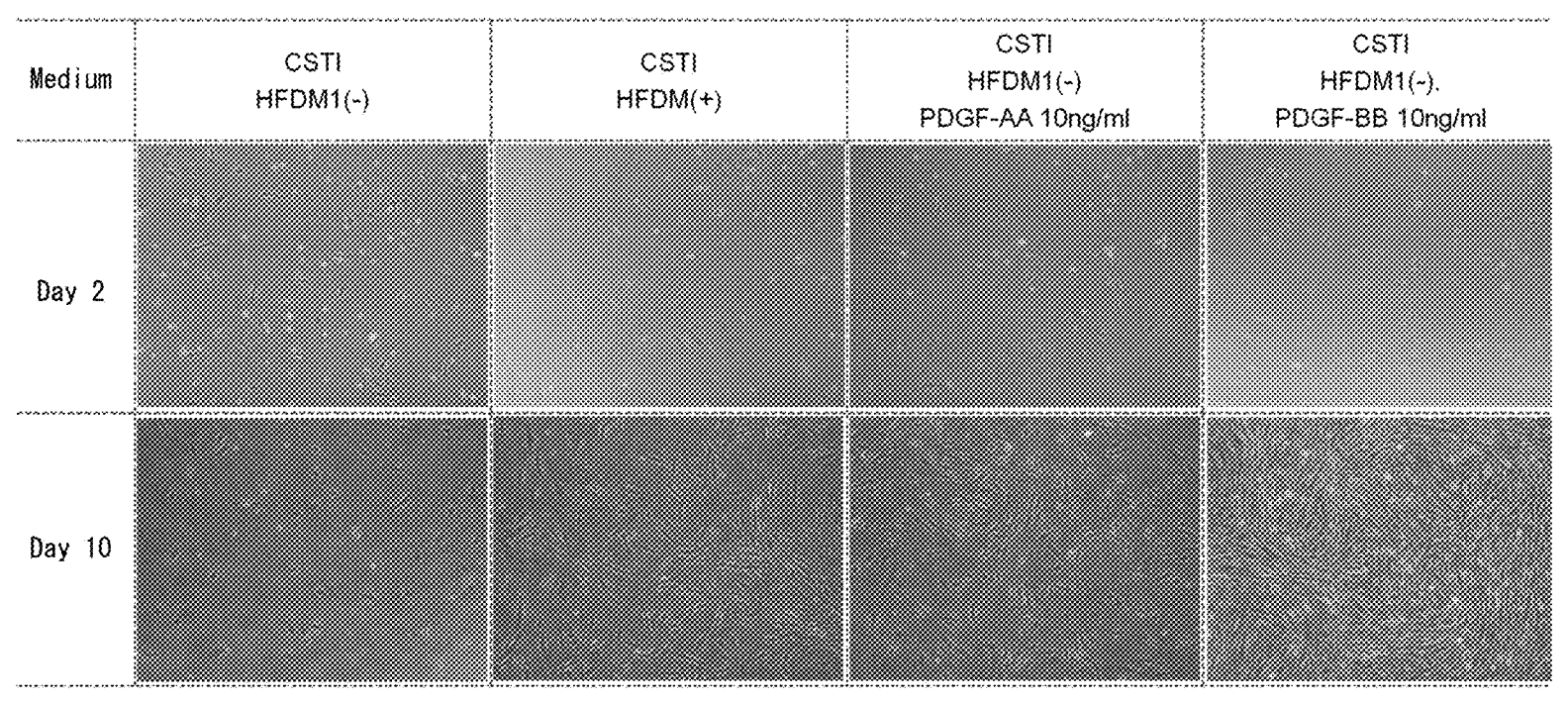

A 12-well plate (BD) was coated with CELLStart™ (Life Technologies), and cryopreserved DS cells (from 21-year-old male scalp, DSC, passage number: 0) were suspended in 1 ml of serum-free medium and seeded on the plate at $4 \times 10^4$ cells per well. The serum-free media used were 1) HFDM-1(−) medium (Cell Science & Technology Institute), 2) HFDM-1(+) medium (Cell Science & Technology Institute), 3) PDGF-AA (10 ng/ml)-dissolved HFDM-1(−) medium and 4) PDGF-BB (10 ng/ml)-dissolved HFDM-1(−) medium. Culturing was conducted at 37° C. in the presence of 5% carbon dioxide gas. The cells were observed under microscopy on days 2, 5 and 10 (FIG. 1: 40×), and the number of cells per visual field was counted (FIG. 2).

Example 2. Growth of DS Cells (Cup Region) Using Serum-Free Medium (StemProSFM CTS/Mosaic hMSC SF Culture)

Figure 4:
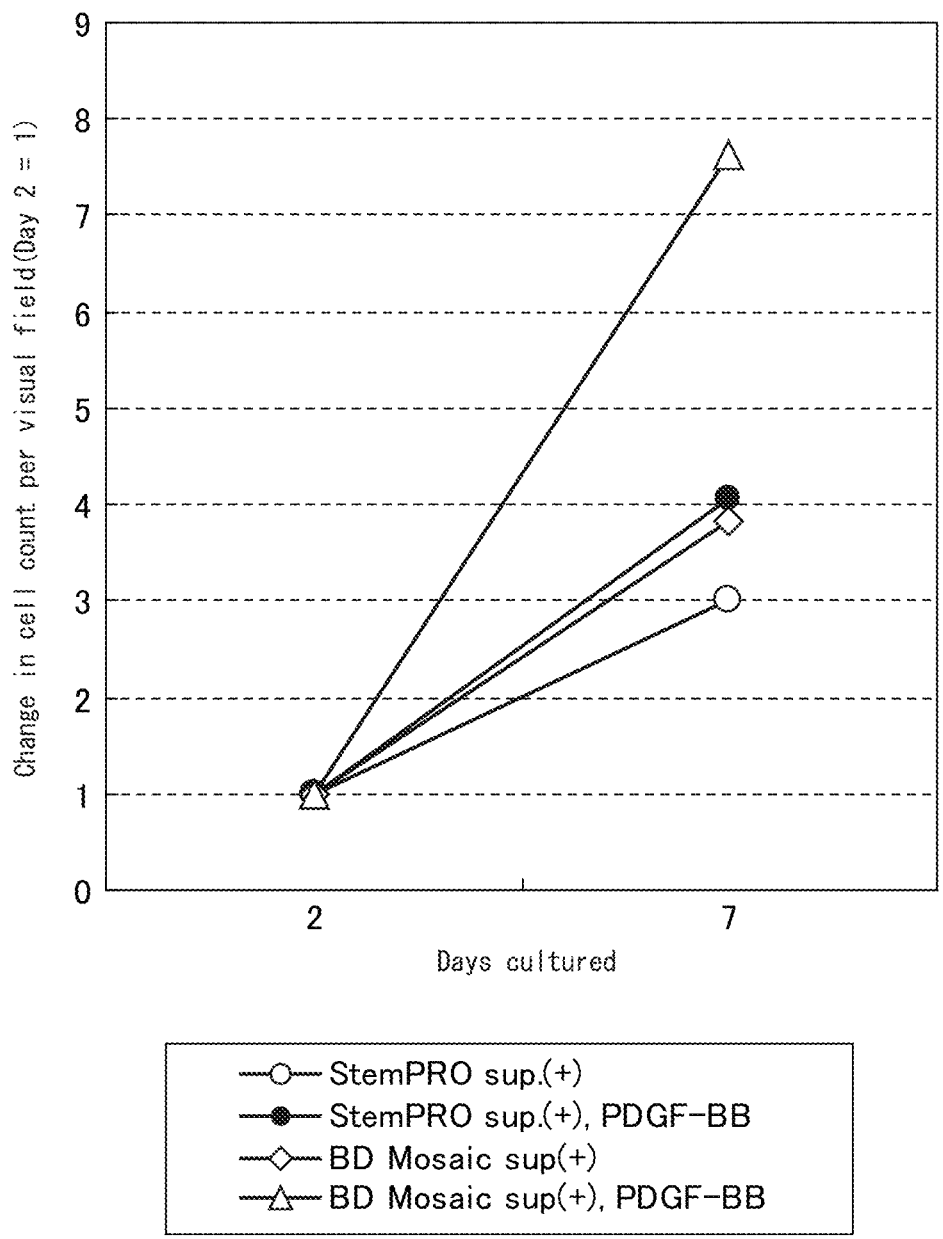
FIG. 4 is a graph showing changes in cell counts of human DS cells cultured using 1) StemProSFM CTS (sup+, Life Technologies), 2) PDGF-BB (10 ng/ml)-dissolved StemProSFM CTS (sup+, Life Technologies), 3) Mosaic hMSC SF Culture Medium (sup+, BD) and 4) PDGF-BB (10 ng/ml)-dissolved Mosaic hMSC SF Culture Medium (sup+, BD), as serum-free media (days 2 and 7).

A 12-well plate (BD) was coated with CELLStart™ (Life Technologies), and cryopreserved DS cells (from 50-year-old male scalp, DSC, passage number: 0) were suspended in 1 ml of serum-free medium and seeded on the plate at $4 \times 10^4$ cells per well. The serum-free media used were 1) StemProSFM CTS (sup+, Life Technologies), 2) PDGF-BB (10 ng/ml)-dissolved StemProSFM CTS (sup+, Life Technologies) and 3) Mosaic hMSC SF Culture Medium (sup+, BD) and 4) PDGF-BB (10 ng/ml)-dissolved Mosaic hMSC SF Culture Medium (sup+, BD). Culturing was conducted at 37° C. in the presence of 5% carbon dioxide gas. The cells were observed under microscopy on days 2 and 7 (FIG. 3: 40×), and the number of cells per visual field was counted (FIG. 4).

Example 3. Growth of DS Cells Using Serum-Free Medium (HFDM-1)

Figure 6:
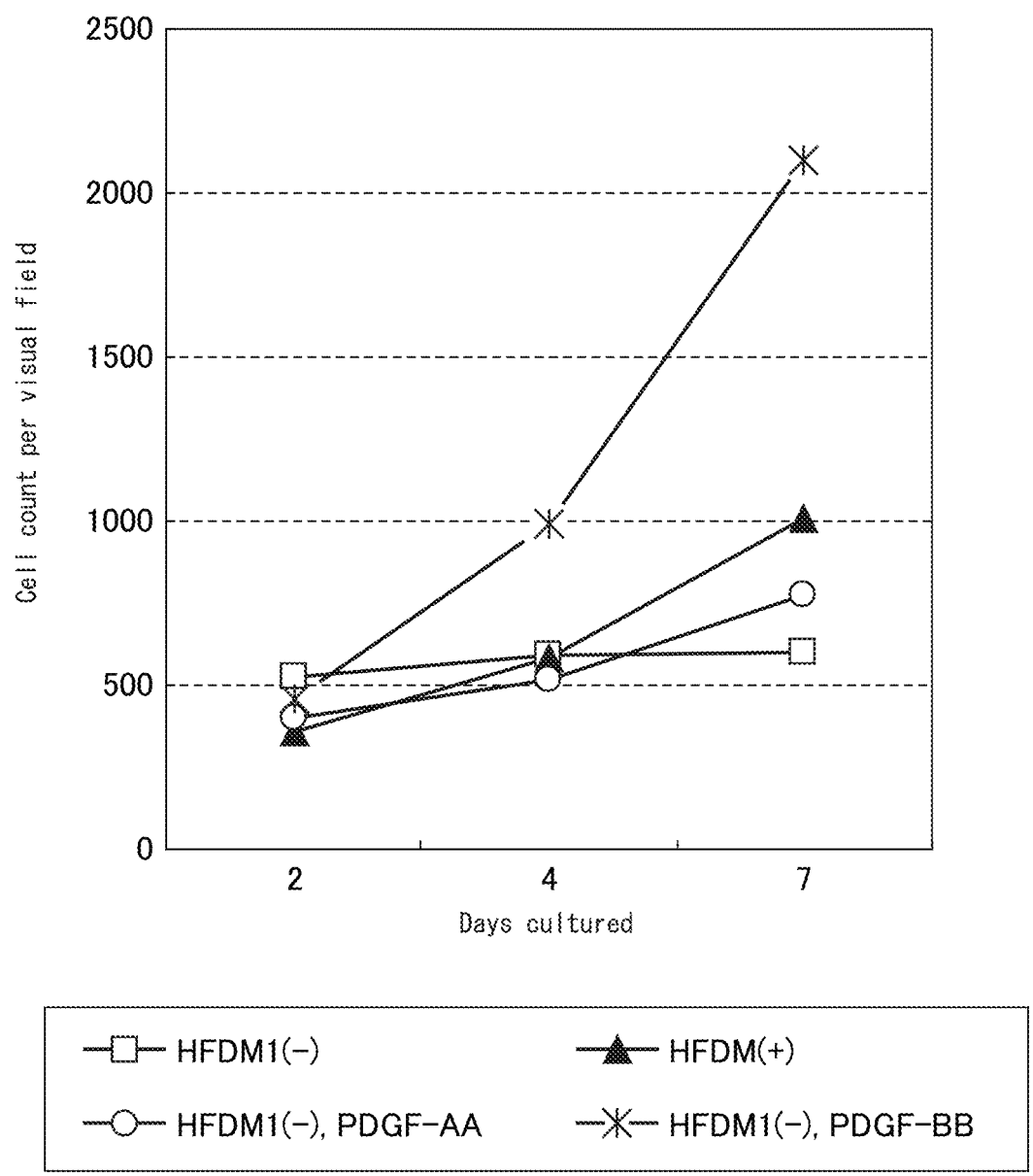
FIG. 6 is a graph showing changes in cell counts of human DS cells cultured using 1) HFDM-1(−) medium, 2) HFDM-1(+) medium, 3) PDGF-AA (10 ng/ml)-dissolved HFDM-1(−) medium and 4) PDGF-BB (10 ng/ml)-dissolved HFDM-1(−) medium, as serum-free media (days 2, 4 and 7).

A 12-well plate (BD) was coated with CELLStart™ (Life Technologies), and cryopreserved DS cells (from 43-year-old male scalp, DS, passage number: 0) were suspended in 1 ml of serum-free medium and seeded on the plate at $4 \times 10^4$ cells per well. The serum-free media used were 1) HFDM-1(−) medium (Cell Science & Technology Institute), 2) HFDM-1(+) medium (Cell Science & Technology Institute), 3) PDGF-AA (10 ng/ml)-dissolved HFDM-1(−) medium and 4) PDGF-BB (10 ng/ml)-dissolved HFDM-1(−) medium. Culturing was conducted at 37° C. in the presence of 5% carbon dioxide gas. The cells were observed under microscopy on days 2, 4 and 7 (FIG. 5: 40×; 4th day not shown), and the number of cells per visual field was counted (FIG. 6).

Example 4. Growth of DS Cells Using Serum-Free Medium (StemProSFM CTS Sup+/StemProSFM CTS Sup−)

Figure 7:
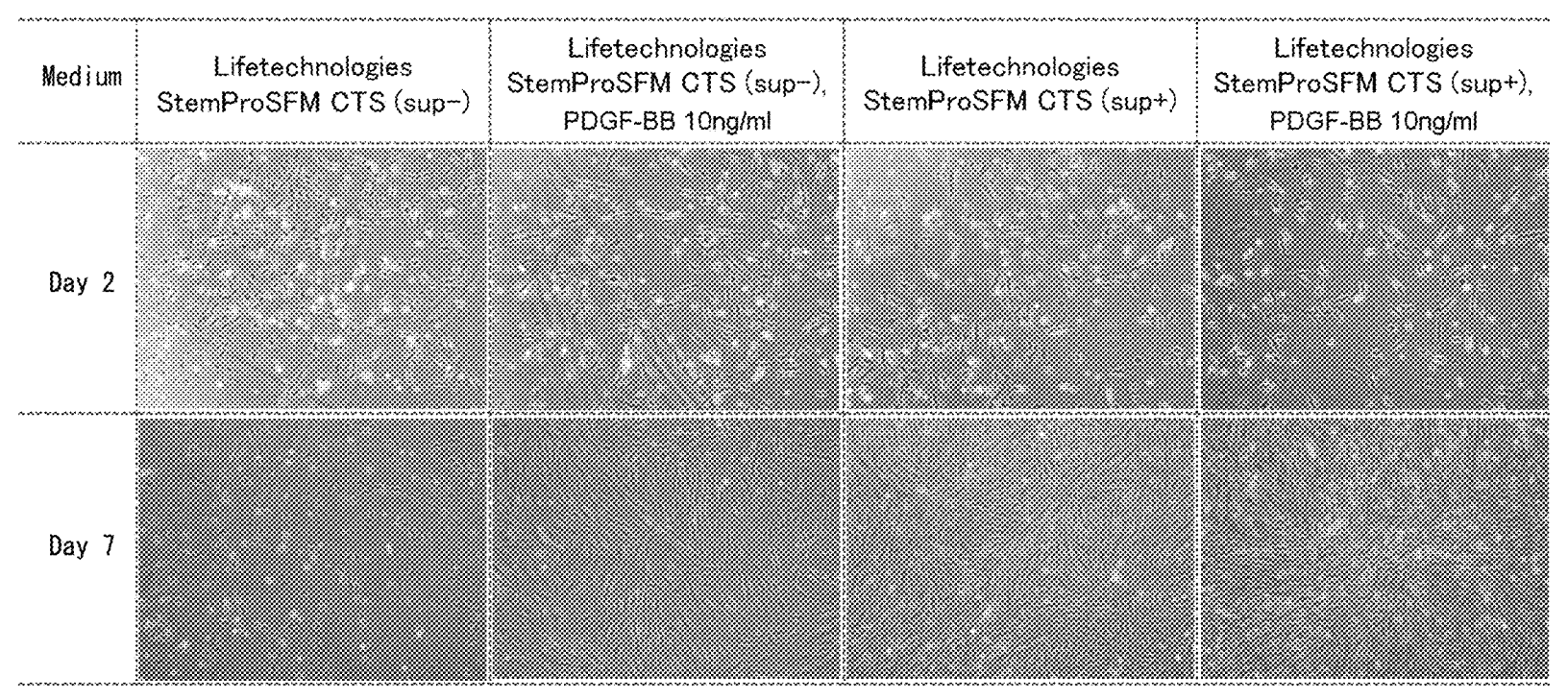
Figure 8:
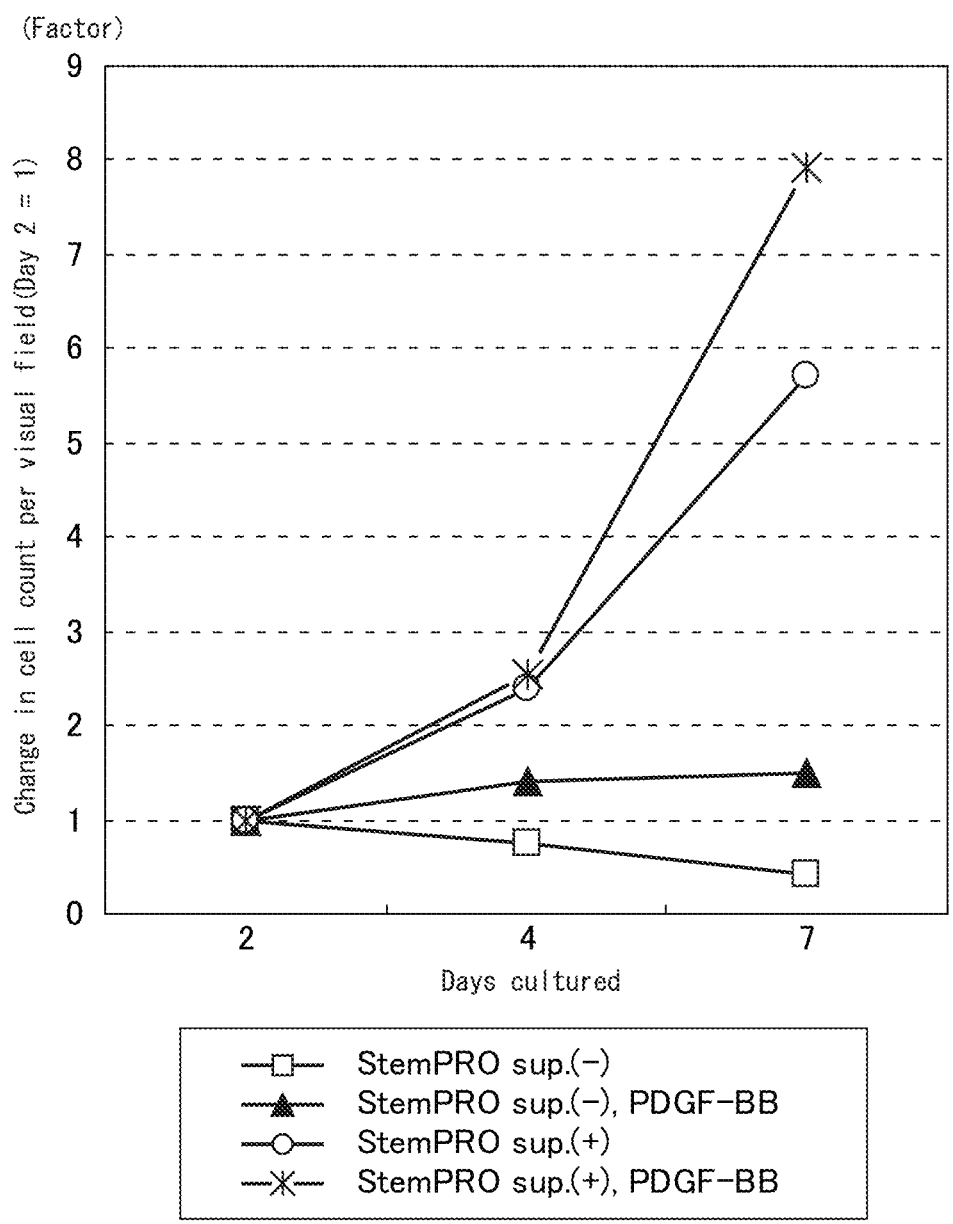
FIG. 8 is a graph showing changes in cell counts of human DS cells cultured using 1) StemProSFM CTS (sup−, Life Technologies), 2) PDGF-BB (10 ng/ml)-dissolved StemProSFM CTS (sup−, Life Technologies), 3) StemProSFM CTS (sup+, Life Technologies) and 4) PDGF-BB (10 ng/ml)-dissolved StemProSFM CTS (sup+, Life Technologies), as serum-free media (days 2, 4 and 7).

A 12-well plate (BD) was coated with CELLStart™ (Life Technologies), and cryopreserved DS cells (from 43-year-old male scalp, DS, passage number: 0) were suspended in 1 ml of serum-free medium and seeded on the plate at $4 \times 10^4$ cells per well. The serum-free media used were 1) StemProSFM CTS (sup−, Life Technologies), 2) PDGF-BB (10 ng/ml)-dissolved StemProSFM CTS (sup−, Life Technologies), 3) StemProSFM CTS (sup+, Life Technologies) and 4) PDGF-BB (10 ng/ml)-dissolved StemProSFM CTS (sup+, Life Technologies). Culturing was conducted at 37° C. in the presence of 5% carbon dioxide gas. The cells were observed under microscopy on days 2, 4 and 7 (FIG. 7: 40×; 4th day not shown), and the number of cells per visual field was counted (FIG. 8).

Example 5. Growth of Fibroblasts Using Serum-Free Medium (StemProSFM CTS Sup+)

Figure 10:
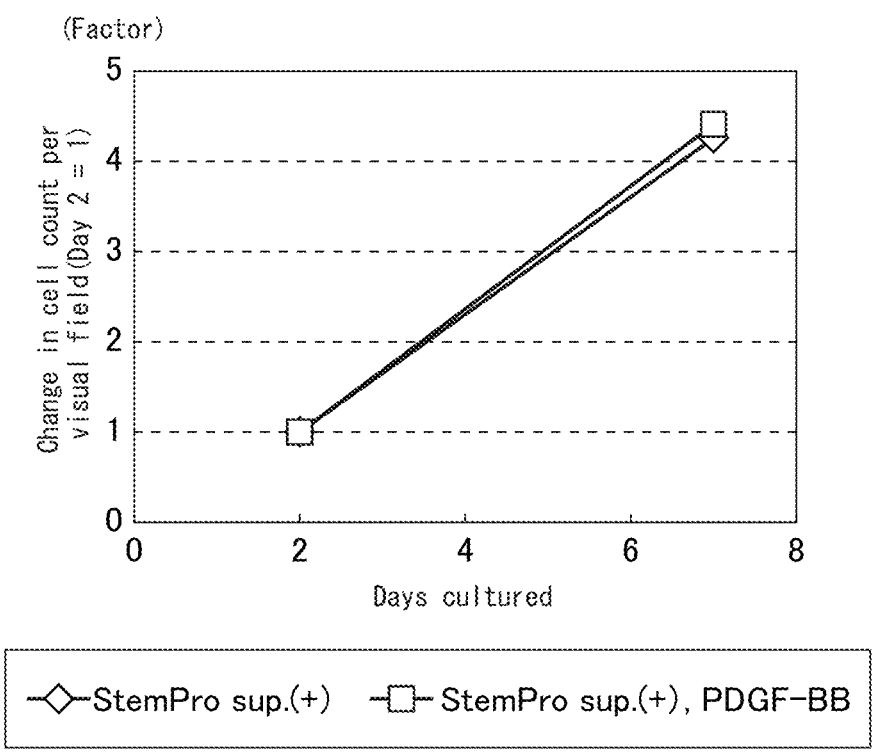
FIG. 10 is a graph showing changes in cell counts of human skin fibroblasts cultured using 1) StemProSFM CTS (sup+, Life Technologies) and 2) PDGF-BB (10 ng/ml)-dissolved StemProSFM CTS (sup+, Life Technologies), as serum-free media (days 2 and 7).

A 12-well plate (BD) was coated with CELLStart™ (Life Technologies), and cryopreserved human skin fibroblasts were suspended in 1 ml of serum-free medium and seeded on the plate at $4 \times 10^4$ cells per well. The serum-free media used were 1) StemProSFM CTS (sup+, Life Technologies) and 2) PDGF-BB (10 ng/ml)-dissolved StemProSFM CTS (sup+, Life Technologies). Culturing was conducted at 37° C. in the presence of 5% carbon dioxide gas. The cells were observed under microscopy on days 2 and 7 (FIG. 9: 40×), and the number of cells per visual field was counted (FIG. 10).

What is claimed is:

1. A method of growing dermal sheath (DS) cells, comprising:
    obtaining isolated DS cells;
    preparing a serum free culture medium comprising a basal medium, the DS cells, and PDGF-BB; and
    growing the DS cells in the prepared serum free culture medium, wherein the isolated DS cells are derived from the dermal sheath cup (DSC) region and wherein the amount of PDGF-BB in the serum free culture medium is from 1 to 10 ng/ml.
2. The method of claim 1, wherein the serum free medium further comprises a Wnt signal activating agent.
3. The method of claim 2, wherein the Wnt signal activating agent is a glycogen synthase kinase-3 (GSK-3) inhibitor activity agent.
4. The method of claim 2, wherein the amount of Wnt signal activating agent is about 0.01 µM to 100 µM.
5. The method of claim 1, wherein said growing the DS cells comprises forming a sphere from the DS cells.
6. The method of claim 1, wherein the DS cells are mammalian DS cells.

* * * * *